(12) United States Patent
Lee et al.

(10) Patent No.: US 6,905,586 B2
(45) Date of Patent: *Jun. 14, 2005

(54) DNA AND RNA SEQUENCING BY NANOSCALE READING THROUGH PROGRAMMABLE ELECTROPHORESIS AND NANOELECTRODE-GATED TUNNELING AND DIELECTRIC DETECTION

(75) Inventors: James W. Lee, Knoxville, TN (US); Thomas G. Thundat, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 419 days.

This patent is subject to a terminal disclaimer.

(21) Appl. No.: 10/055,881

(22) Filed: Jan. 28, 2002

(65) Prior Publication Data

US 2003/0141189 A1 Jul. 31, 2003

(51) Int. Cl.[7] .......................... C12Q 1/68; G01N 27/26
(52) U.S. Cl. ...................... 204/600; 204/450; 204/452; 204/453; 204/603; 204/604; 204/643; 204/547; 435/6; 435/287.2
(58) Field of Search ................................. 204/600, 450, 204/452, 453, 604, 603, 643, 547; 435/6, 287.2

(56) References Cited

U.S. PATENT DOCUMENTS

| | | | |
|---|---|---|---|
| 6,447,663 B1 * | 9/2002 | Lee et al. | 205/104 |
| 6,755,956 B2 * | 6/2004 | Lee et al. | 205/104 |
| 6,763,705 B1 * | 7/2004 | Thundat et al. | 73/64.53 |
| 2003/0127333 A1 * | 7/2003 | Lauks et al. | 204/600 |
| 2003/0157698 A1 * | 8/2003 | Thundat et al. | 435/287.2 |
| 2003/0211502 A1 * | 11/2003 | Sauer et al. | 435/6 |
| 2004/0124084 A1 * | 7/2004 | Lee et al. | 204/600 |

OTHER PUBLICATIONS

J.J. Kasianowicz, et. al., "Characterization of Individual Polynucleotide Molecules Using a Membrane Channel," Proc. Natl. Acad. Sci. USA, vol., 93, pp. 13770–13773, Nov. 1996.

M. Akeson, et. al., "Microsecond Time–Scale Discrimination Among Polycytidylic Acid, Polyadenylic Acid, and Polyuridylic Acid as Homopolymers or as Segments Within Single RNA Molecules," Biophysical Journal, vol. 77, pp. 3227–3233, Dec. 1999.

* cited by examiner

Primary Examiner—Alan Diamond
(74) Attorney, Agent, or Firm—James M Spicer

(57) ABSTRACT

An apparatus and method for performing nucleic acid (DNA and/or RNA) sequencing on a single molecule. The genetic sequence information is obtained by probing through a DNA or RNA molecule base by base at nanometer scale as though looking through a strip of movie film. This DNA sequencing nanotechnology has the theoretical capability of performing DNA sequencing at a maximal rate of about 1,000,000 bases per second. This enhanced performance is made possible by a series of innovations including: novel applications of a fine-tuned nanometer gap for passage of a single DNA or RNA molecule; thin layer microfluidics for sample loading and delivery; and programmable electric fields for precise control of DNA or RNA movement. Detection methods include nanoelectrode-gated tunneling current measurements, dielectric molecular characterization, and atomic force microscopy/electrostatic force microscopy (AFM/EFM) probing for nanoscale reading of the nucleic acid sequences.

44 Claims, 13 Drawing Sheets

FIG. 5 - - Prior Art ac Phase Shift $\theta = \tan^{-1}\left(\frac{1}{\omega RC}\right)$ $V_1 = V_{01} \cos \omega t$
$V_2 = V_{02} \cos(\omega t + \theta)$

DNA AND RNA SEQUENCING BY NANOSCALE READING THROUGH PROGRAMMABLE ELECTROPHORESIS AND NANOELECTRODE-GATED TUNNELING AND DIELECTRIC DETECTION

STATEMENT REGARDING FEDERALLY SPONSORED RESEARCH OR DEVELOPMENT

The United States Government has rights in this invention pursuant to Contract No. DE-AC05-00OR22725 between the United States Department of Energy and UT-Battelle, LLC.

BACKGROUND OF THE INVENTION

1. Field of the Invention

The invention relates to nucleic acid (DNA and/or RNA) sequencing on a single molecule. More particularly, it relates to obtaining the genetic sequence information by direct reading of a DNA or RNA molecule base by base at nanometer scale as though looking through a strip of movie film.

2. Background Information

A key step in the present invention is the ability to fabricate a required nanometer-scale gap that is defined as the distance between a pair of sharp nanoelectrode tips. Such a gap is used in the present invention as a nucleotide (base) detection gate. The following is a description of our recent invention for accomplishing the construction of such a nanogap.

Nanometer-scale modification of nanostructures can be carried out in liquids at ambient temperature and neutral pH through electric field-directed, programmable, pulsed electrolytic metal deposition or depletion. The use of pulsed current is a critical feature in the method, while temperature and pH are not critical parameters.

Application of a programmable and short—time scale of nanosecond (ns) to millisecond (ms)—pulsing direct current source is used to control the number of atoms being deposited by the electrolytic metal reduction and deposition process. As shown in the following platinum deposition reaction at a cathode using water-soluble hexachloroplatinate, the number of electrons supplied can control the formation of metallic platinum. In electrolytic deposition, electric current and the duration of the current can control the number of electrons.

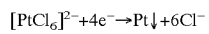

$$[PtCl_6]^{2-} + 4e^- \rightarrow Pt\downarrow + 6Cl^-$$

Other water-soluble metal compounds that have been shown to be applicable include, but are not limited to the following: $PtCl_4$, $OsCl_3$, $Na_2[PtCl_6]$, $Na_2[OsCl_6]$, $(NH_4)_2RuCl_6$, $K_3RuCl_6$, $Na_2PdCl_6$, $Na_2IrCl_6$, $(NH_4)_3IrCl_6$, $(NH_4)_3RhCl_6$, $K_2PdCl_4$, $(NH_4)_2PdCl_4$, $Pd(NH_3)_4Cl_2$, $ReCl_3$, $NiCl_2$, $CoCl_2$, $PtO_2$, $PtCl_2$, $Pt(NH_3)_4Cl_2$, $CuSO_4$, $(NH_4)_6Mo_7O_{24}$, $NaAuCl_4$, $K_2[PtCl_4]$, and $K_3Fe(CN)_6$. Combinations of two or more water-soluble metal compounds can be used sequentially or simultaneously.

As illustrated in FIG. 1, an embodiment of our recent invention involves a special utilization of a programmable current source 18 that can precisely control the number of electrons used to achieve the desired nanometer-scale electrolytic metal deposition. A nonconductive substrate 10 supports nanometer-sized electrodes, also called nanowires and nanoelectrodes (cathode 12 and anode 14) which are usually comprised of gold but can be other metals or conductive materials. A spacing between the nanoelectrode tips 13, 15 in the range of 1 μm to 10 μm produces good results.

A preselected metal 16 is deposited onto the tip of the cathode 12. The metal 16 is usually Pt, but can be any metal that can be deposited electrolytically. The programmable, pulsable current source 18 has electrical connections 20, 22 to the respective nanoelectrodes 12, 14. A bypass circuit 24, which includes a bypass selector switch 26 and a variable resistor 28, is also shown.

The nanoelectrodes 12, 14 represent a subset of microscopic sized structures (nanostructures) that are suitable for use. Nanostructures acting as electrodes can be of various sizes and shapes. Spacing between the two nanostructures should not exceed 50 μm. Preferably, the spacing is 20 μm or less, more preferably 10 μm or less, and most preferably, 1 μm or less.

The programmable, pulsable current source 18 can be of any suitable construction. Keithley Model 220 programmable current source or the latest Keithley Model 2400 series of Source Meters (available from Keithley Instruments, Inc., 28775 Aurora Road, Cleveland, Ohio 44139, or on the Internet at www.keithley.com) are already capable of supplying a minimum of about 9400 electrons per pulse [500 fA×3 ms×electron/($1.60×10^{-19}$ C)]. This could translate to a deposition of 2350 platinum atoms per pulse based on the stoichiometry of the deposition reaction. If this amount of platinum is deposited on the end of a nanowire with a 10- by 10-nm cross section, 2350 platinum atoms per pulse can translate into about 1 nm of metal deposition (2.6 layers of platinum atoms) per pulse. The programmable, pulsable current source 18 should be capable of controlling the process so that nanometer metal deposition or depletion as precise as about 1500 metal 16 atoms per pulse can be achieved. A preferable range is contemplated to be 1500 to $10^{14}$ atoms per pulse, although operation is possible well beyond this range.

The bypass circuit 24 is preferably added to fine-tune the electron flow for even more precise control of deposition or depletion, i.e., the addition or removal of monolayers or submonolayers of atoms, that can be achieved. The bypass circuit 24 is used to divert some of the electricity away from the nanoelectrodes 12, 14 in order to deposit or deplete fewer metal atoms per pulse. For example, when the impedance of the variable resistor 28 is adjusted to 50% of the impedance between the two nanoelectrodes 12, 14, two thirds of the 9400 electrons per pulse can be drained through the bypass circuit 24. In this case, the electrolytic metal deposition can be controlled to a step as precise as 780 platinum atoms (3130 electrons) per pulse. This translates to a deposition of 0.87 layer of platinum atoms 16 on a 10- by 10-nm surface at the tip of the cathodic nanoelectrode 12. By allowing a greater portion of the current to flow through the bypass circuit 24, it is possible to control deposition of metal 16 atoms as precise as 100 atoms per pulse. A preferable range for this extremely finely controlled deposition is contemplated to be 100–2500 atoms per pulse, although operation is possible well beyond this ultrafine deposition range.

The bypass circuit 24 can also protect the nanometer structure from electrostatic damage, especially when the structure is dry. For example, after desired programmable electrolytic metal deposition is achieved as illustrated in FIG. 1, the bypass circuit 24 should remain connected with the nanostructures 12 and 14 while the programmable pulsing current source can then be removed. As long as the bypass circuit remains connected with the nanostructures 12 and 14, any electrostatic charges that might be produced during wash and dry of the nanostructures will be able to flow through the bypass circuit 24. The bypass circuit 24 comprises the closed switch 26, the variable resistor 28, and wires that connect the switch 26 and the variable resistor 28 with the nanoelectrodes 12, 14. This prevents accumulation of electrostatic charges at any one of electrodes against the other electrode from occurring, thus eliminating the possibility of electrostatic damage at the nanometer gap between the tips 13, 15 of the nanoelectrodes 12, 14.

A special nanostructural arrangement can be used to control the initiation point(s) of nanometer bonding. Special structural arrangements of the nanowire electrodes can now be made by various lithographic techniques to control the initiation point(s) of the electrolytic metal deposition. As shown in FIG. 2, multiple nanowire cathodes 12, 12' should have respective tips 13, 13' pointing to the respective tips 15, 15' of nanowire anode 14 so that the strongest electric field is therebetween. Spacing of the multiple nanowire cathodes 12, 12' should be regulated to ensure deposition of metal 16, 16' at the desired cathode location, because the electric field (E) is a vector that is strongly dependent on distance (r):

$$E \propto r^{-2}.$$

Electrolytic metal-dissolving reactions are applied to deplete metal, that is, to open nanometer gaps and control gap size as shown in FIG. 3. By conducting the reversal of the metal deposition reaction with sodium chloride solution instead of hexachloroplatinate as an electrolytic substrate, metallic platinum at the anode tip 16 can be electrolytically depleted via dissolution in a controllable way according to the following reaction:

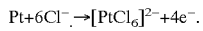
$$Pt+6Cl^- \rightarrow [PtCl_6]^{2-}+4e^-.$$

This metal-dissolution reaction should also be able to control the gap size between the nanoelectrode tips 13, 15. The site and the extent of electrolytic metal depletion can also be controlled by proper selection of the desired polarity of the electric field and by use of a programmable current source with a bypass circuit, as described herein.

The salient features, as described hereinabove, may be applied in full, in part, or in any combination. Any number of nanostructures can be simultaneously bonded or dissolved on a particular substrate.

The nanostructure to be metal-deposited does not have to be metal. Any conductive nanowires such as, for example, nanotubes (especially carbon nanotubes), can be connected because of their capability for nanometer electrolytic metal deposition.

For metal depletion, the nonmetallic ions do not have to be $Cl^-$. Any anions, such as $F^-$ and $CN^-$, that can electrolytically dissolve metals (Pt, Pd, Au, etc.) may be used as alternative versions.

The above description is from our recently filed patent application entitled "Programmable Nanometer-Scale Electrolytic Metal Deposition and Depletion"; by James W. Lee and Elias Greenbaum; U.S. patent application Ser. No. 09/694,978; filed Oct. 24, 2000, now U.S. Pat. No. 6,447,663.

The following is a description of some of the structures and properties of DNA and RNA molecules. DNA is a polymer of deoxyribonucleotides. A nucleotide consists of a nitrogenous base, a sugar, and one or more phosphate groups. The sugar in a deoxyribonucleotide is deoxyribose. The nitrogenous base is a derivative of purine or pyrimidine. The purines in DNA are adenine (A) and guanine (G), and the pyrimidines are thymine (T) and cytosine (C).

The backbone of DNA, which is invariant throughout the molecule, consists of deoxyriboses linked by phosphate groups. Specifically, the 3'-hydroxyl of the sugar moiety of one deoxyribonucleotide is joined to the 5'-hydroxyl of the adjacent deoxyribose (sugar) by the phosphodiester bridge. The variable part of the DNA is its sequence of four distinct bases (A, G, C, and T), which carries genetic information. A part of a single-stranded DNA molecule is illustrated in FIG. 4. Under in vivo conditions, most naturally occurring DNA molecules are in double-helix forms (FIG. 5).

In 1953, James Watson and Francis Crick first deduced the three-dimensional structure of DNA. The important features of their model of DNA are as follows:

1. Two helical polynucleotide chains are coiled around a common axis. The chains run in opposite directions (FIG. 5, bottom).
2. The purine and pyrimidine bases are on the inside of the helix, whereas the phosphate and deoxyribose units are on the outside. The planes of the bases are perpendicular to the helix axis. The planes of the sugars are nearly at right angles to those of the bases.
3. The diameter of the helix is 2.0 nm. Adjacent bases are separated by 0.34 nm along with the helix axis and related by a rotation of 36°. Hence, the helical structure repeats after ten residues on each chain, that is, at intervals of 3.4 nm.
4. The two chains are held together by hydrogen bonds between pairs of bases. Adenine is always paired with thymine; guanine is always paired with cytosine (FIG. 5, top).

DNA molecules can be cut into short pieces with a number of restriction enzymes at specific sites. Furthermore, the two strands of a DNA helix readily come apart when the hydrogen bonds between its paired bases are disrupted. This process can be accomplished by heating a solution of DNA or by adding acid or alkali to ionize its bases. Under certain other solvent conditions, the two chains of a double-stranded DNA molecule can dissociate into a single-stranded DNA molecule, which may sometimes be more convenient for DNA sequencing analysis. Separated complementary strands of DNA can spontaneously reassociate to form a double helix when the temperature is lowered below the melting point. It is a common practice to use urea solution to keep single-stranded DNA molecules from annealing.

RNA (ribonucleic acid), like DNA, is a long, unbranched polymer consisting of nucleotides jointed by 3'→5' phosphodiester bonds. The covalent structure of RNA differs from that of DNA in two respects. As indicated by their name, the sugar units in RNA are riboses rather than deoxyriboses. Ribose contains a 2'-hydroxyl group not present in deoxyribose. The other difference is that one of the four major bases in RNA is uracil (U) instead of thymine (T). Although uracil, like thymine, can form a base pair with adenine, it lacks the methyl group present in thymine. RNA molecules car be single stranded or double stranded. RNA cannot form a double helix of the B-DNA type because of steric interference by the 2'-hydroxyl groups of its ribose units. However, RNA can adopt a modified double-helical form in which the base pairs are tilted about 20° from the perpendicular to the helix axis, a structure like that of A-DNA.

In some viruses, genes are made of RNA. Other RNA molecules are messenger RNAs (mRNAs), transfer RNAs (tRNAs), and ribosomal RNAs (rRNAs). The tRNAs and rRNAs are part of the protein-synthesis machinery. The mRNAs are the information-carrying intermediates in protein synthesis. In the gene expression of all organisms, the genetic information of DNA is first transcribed into mRNA, which is then translated into protein. Consequently, DNA is not the direct template for protein synthesis. Rather, the template for protein synthesis is mRNA. Therefore, an effective and rapid RNA sequencing technology is also valuable.

There have been significant demand and research activities for development of new sequencing technologies. By measurement of ionic current passing through single ion channels in a lipid bilayer membrane, it has been demonstrated that an electric field can drive single-stranded DNA and RNA molecules through a 2.6 nm membrane pore (Proc. Natl. Acad. Sci. USA Vol. 93, pp. 13770–13773, November 1996). It was further postulated that by measuring the transient blockades of the ion current across the lipid bilayer membrane when a single-stranded DNA or RNA molecule passing through a hemolysin channel that was embedded in the membrane, one might be able to obtain the genetic sequence information of the nucleic acid molecule (Biophysical Journal Vol. 77, pp. 3227–3233, December 1999). We here present a new invention on DNA and/or RNA sequencing that is very different from these earlier approaches.

BRIEF SUMMARY OF THE INVENTION

In accordance with one aspect of the present invention, a nanoscale nucleic acid sequence detection apparatus includes a hydrophilic nonconductive substrate serving as a sample plate; a cathode macroelectrode located on one surface of the substrate; an anode macroelectrode located on the surface of the substrate such that the spacing between the cathode macroelectrode and the anode macroelectrode is greater than the length of one nucleic acid molecule, the spacing between the cathode macroelectrode and the anode macroelectrode defining a nucleic acid loading and delivery path; a molecular transport liquid located on the surface of the substrate; an injection device capable of introducing a sample nucleic acid molecule into the molecular transport liquid; a programmable pulse generator connected to the cathode macroelectrode and the anode macroelectrode, the programmable pulse generator capable of controllably moving a nucleic acid molecule contained in the liquid along the nucleic acid loading and delivery path between the cathode macroelectrode and the anode macroelectrode by means of a programmable electrophoresis electric field; a first nanoelectrode located on the surface of the substrate; a second nanoelectrode located on the surface of the substrate such that the gap between the first nanoelectrode and the second nanoelectrode crosses the nucleic acid loading and delivery path, the gap between the first nanoelectrode and the second nanoelectrode defining a nanometer-size nucleic acid detection gate on the hydrophilic nonconductive substrate; a first nonhydrophilic and nonconductive protective insulating shield constructed on the surface of the substrate along the sides of the first nanoelectrode, the construction of the first protective insulating shield such that only the tip of the first nanoelectrode remains exposed on the surface of the substrate; a second nonhydrophilic and nonconductive protective insulating shield constructed on the surface of the substrate along the sides of the second nanoelectrode, the construction of the second protective insulating shield such that only the tip of the second nanoelectrode remains exposed on the surface of the substrate; and a nucleic acid nucleotide base detection means located at the nucleic acid detection gate.

In accordance with another aspect of the present invention, a nanoscale nucleic acid sequence detection apparatus includes a hydrophobic and nonconductive substrate serving as a sample plate; a cathode macroelectrode located on one surface of the substrate; an anode macroelectrode located on the surface of the substrate such that the spacing between the cathode macroelectrode and the anode macroelectrode is greater than the length of one nucleic acid molecule, the spacing between the cathode macroelectrode and the anode macroelectrode defining a nucleic acid loading and delivery path; a first nanoelectrode located on the surface of the substrate; a second nanoelectrode located on the surface of the substrate such that the gap between the first nanoelectrode and the second nanoelectrode crosses the nucleic acid loading and delivery path, the gap between the first nanoelectrode and the second nanoelectrode defining a nanometer-size nucleic acid detection gate on the hydrophobic and nonconductive substrate; a hydrophilic sample loading and delivery area on the hydrophobic and nonconductive substrate, the hydrophilic area extending along the nucleic acid loading and delivery path from the cathode macroelectrode to the anode macroelectrode, the hydrophilic sample loading and delivery area constructed so as to taper gradually less from the cathode macroelectrode to the nucleic acid detection gate; a molecular transport liquid located on the hydrophilic sample loading and delivery area, the molecular transport liquid preferentially tending to form a funnel-like liquid delivery path on the hydrophilic sample loading and delivery area; an injection device capable of introducing a sample nucleic acid molecule into the molecular transport liquid; a nucleic acid nucleotide base detection means located at the nucleic acid detection gate; a first programmable pulse generator connected to the cathode macroelectrode and to the anode macroelectrode, the first programmable pulse generator capable of controllably moving a nucleic acid molecule contained in the liquid along the nucleic acid loading and delivery path between the cathode macroelectrode and the anode macroelectrode by means of a programmable electrophoresis electric field; two parallel spaced-apart electrically conductive plates, the electrically conductive plates arranged such that the sample plate is located between the electrically conductive plates; and a second programmable pulse generator connected to the electrically conductive plates, the second programmable pulse generator capable of applying a holding electric field across the electrically conductive plates in order to orient the nucleic acid molecule contained in the liquid with respect to the sample plate and the electrically conductive plates.

DETAILED DESCRIPTION OF THE INVENTION

The present invention relates to an apparatus and method for nucleic acid (DNA or RNA) sequencing on a single molecule. More particularly, it relates to obtaining the genetic sequence information by direct reading of a DNA or RNA molecule base by base at nanometer scale, as though looking through a strip of movie film.

The new DNA/RNA sequencing technology has the potential to be at least about 2800 times faster than current methods. Theoretically, the invention has the potential capability of performing DNA sequencing at a maximal rate of about 1,000,000 bases per second per detection system. This enhanced performance is made possible by the series of innovations described herein. These include novel applications of fine-tuned nanometer gaps for passage of a single DNA or RNA molecule; thin layer microfluidics for sample loading and delivery; programmable electric fields for precise control of DNA or RNA movement, etc. Measurement methods include nanoelectrode-gated tunneling current measurement, dielectric molecular characterization, and atomic force microscopy/electrostatic force microscopy (AFM/EFM) probing for nanoscale reading of nucleic acid sequences.

Figure 1:
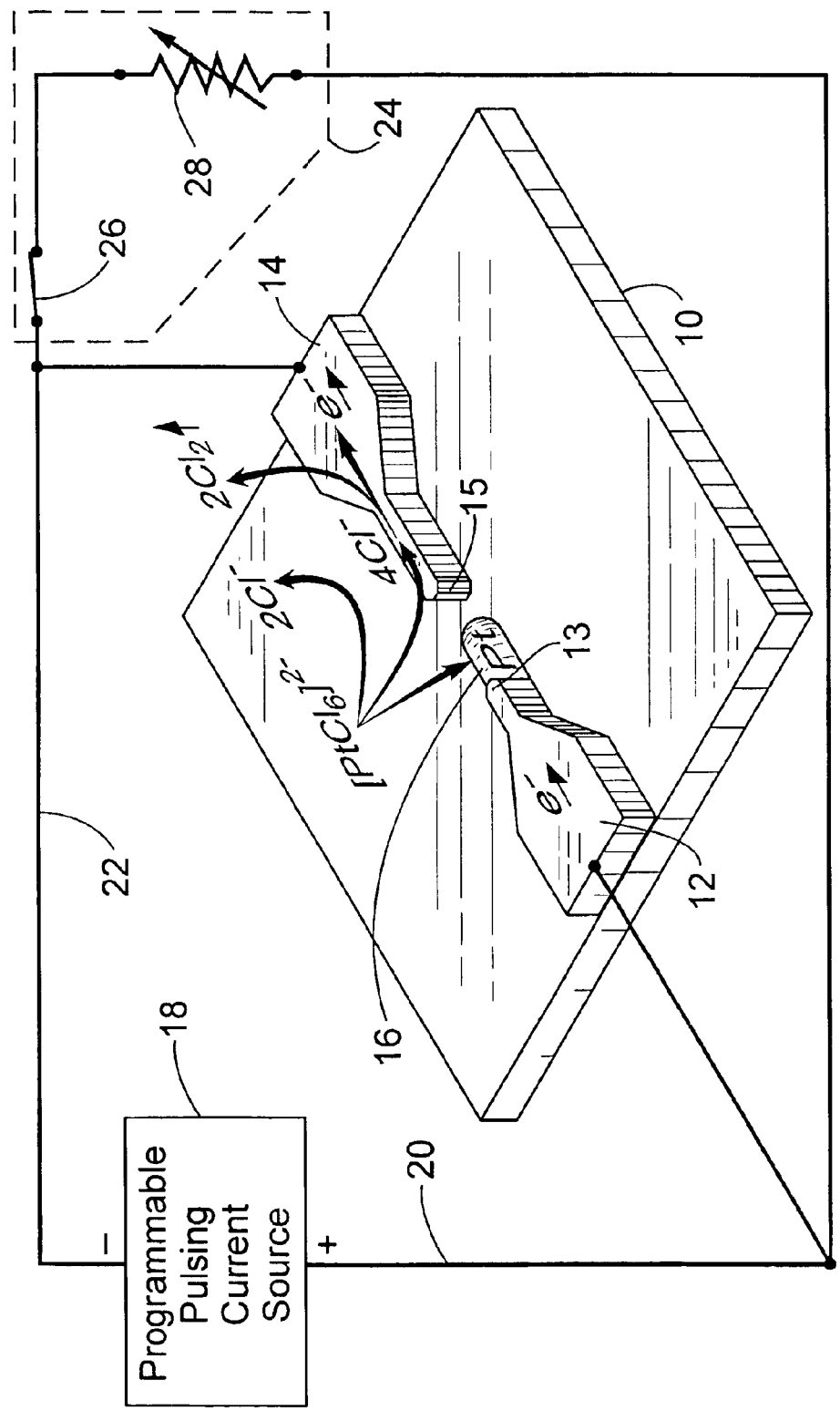
FIG. 1 is an illustration of nanogap manipulation through precision electrolytic deposition of platinum (Pt) on a gold nanostructure in accordance with the present invention.
Figure 2:
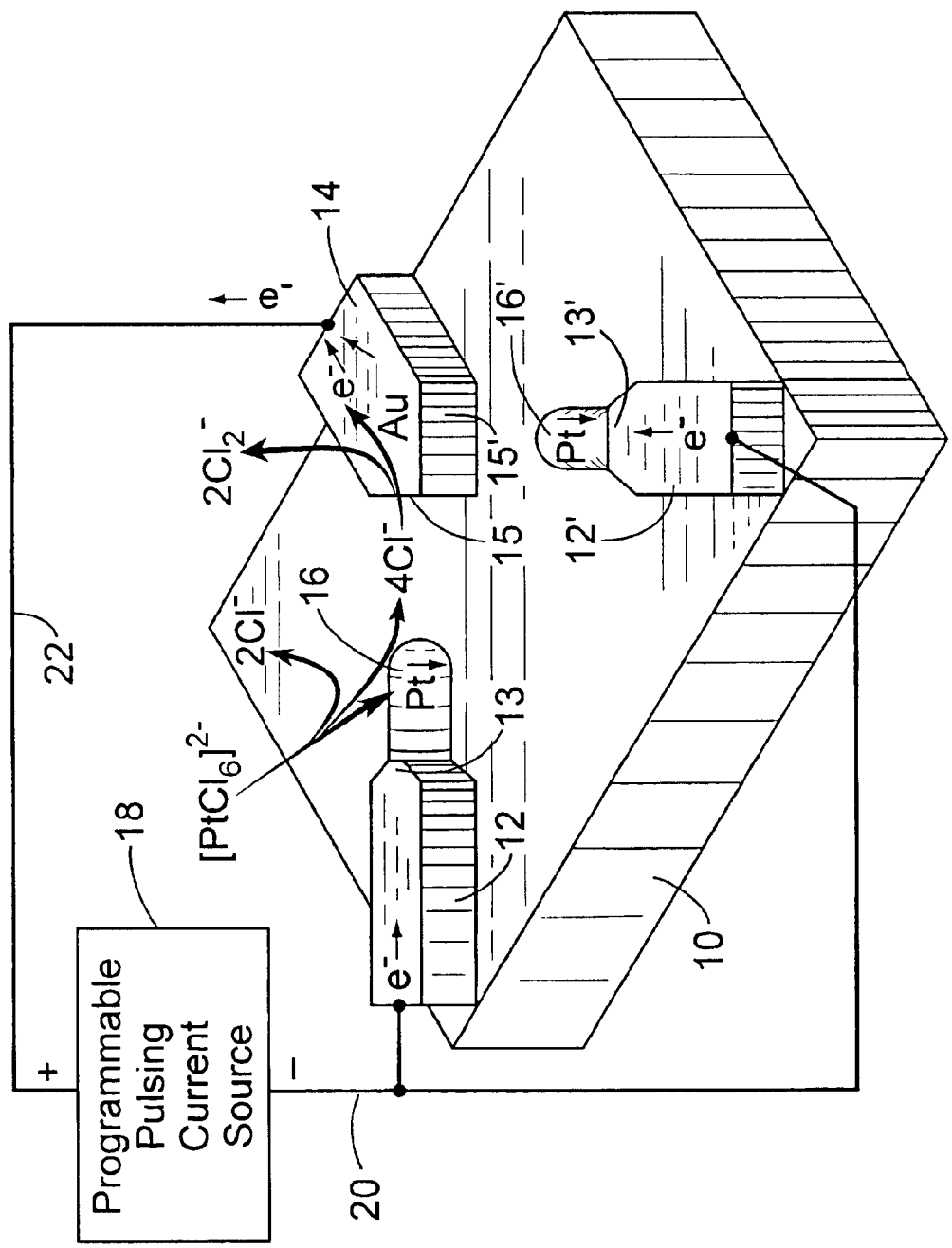
FIG. 2 is an illustration of nanogap modification through deposition of platinum (Pt) on multiple gold nanostructures in accordance with the present invention.
Figure 3:
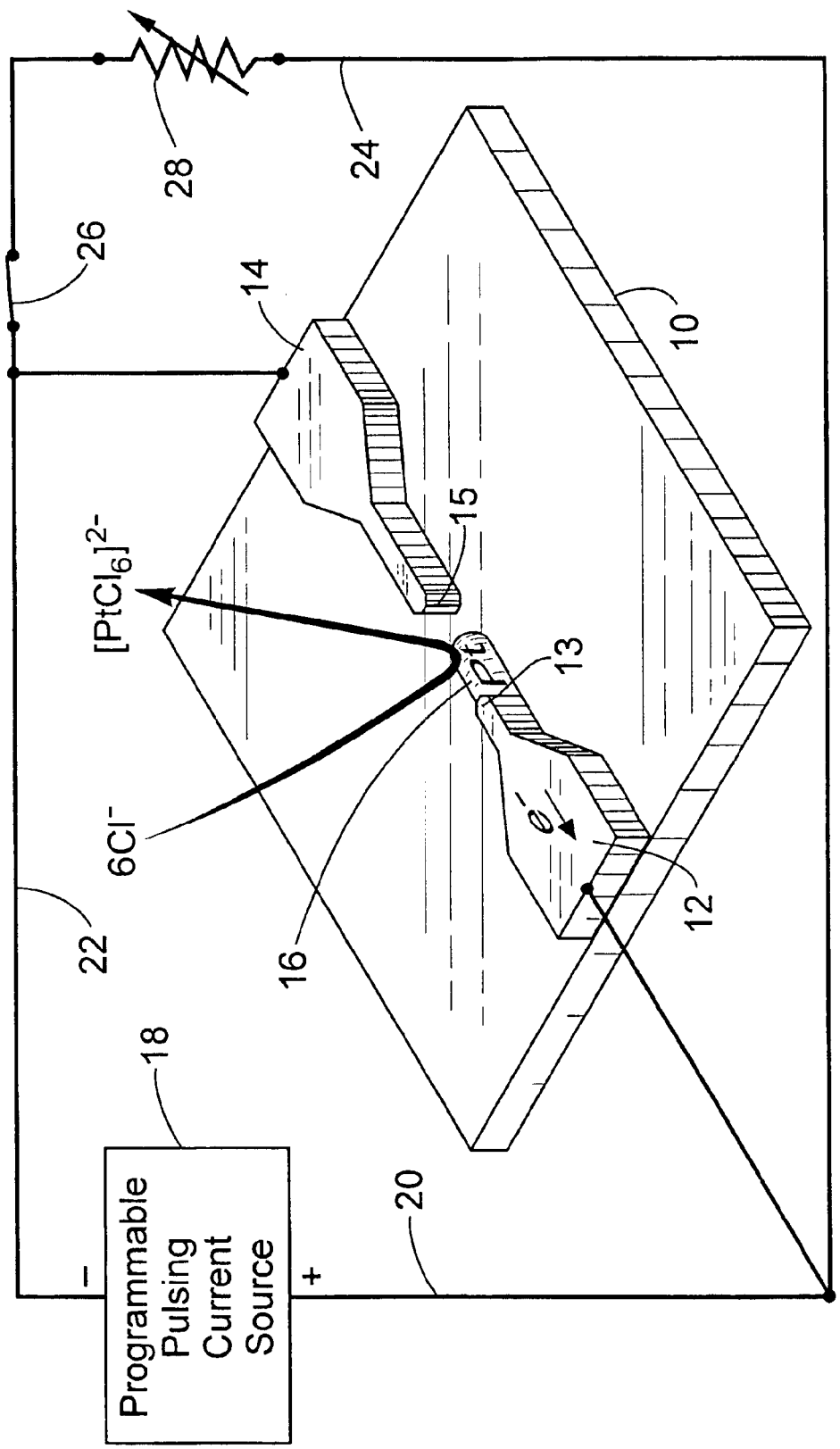
FIG. 3 is an illustration of nanogap modification through depletion of platinum (Pt) from a gold nanostructure in accordance with the present invention.
Figure 4:
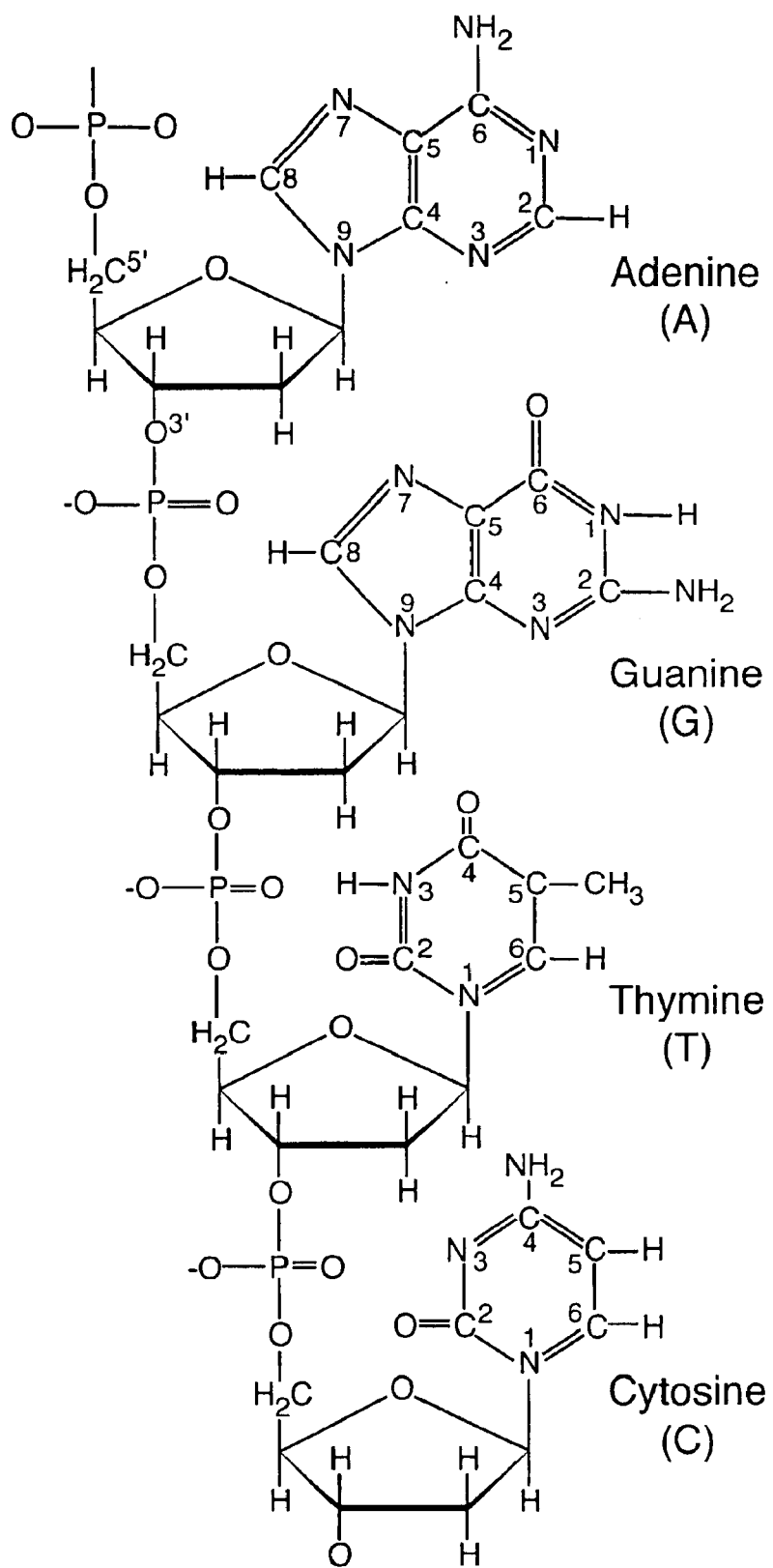
FIG. 4 is an illustration of the chemical structure for a section of a single-stranded DNA molecule.
Figure 5:
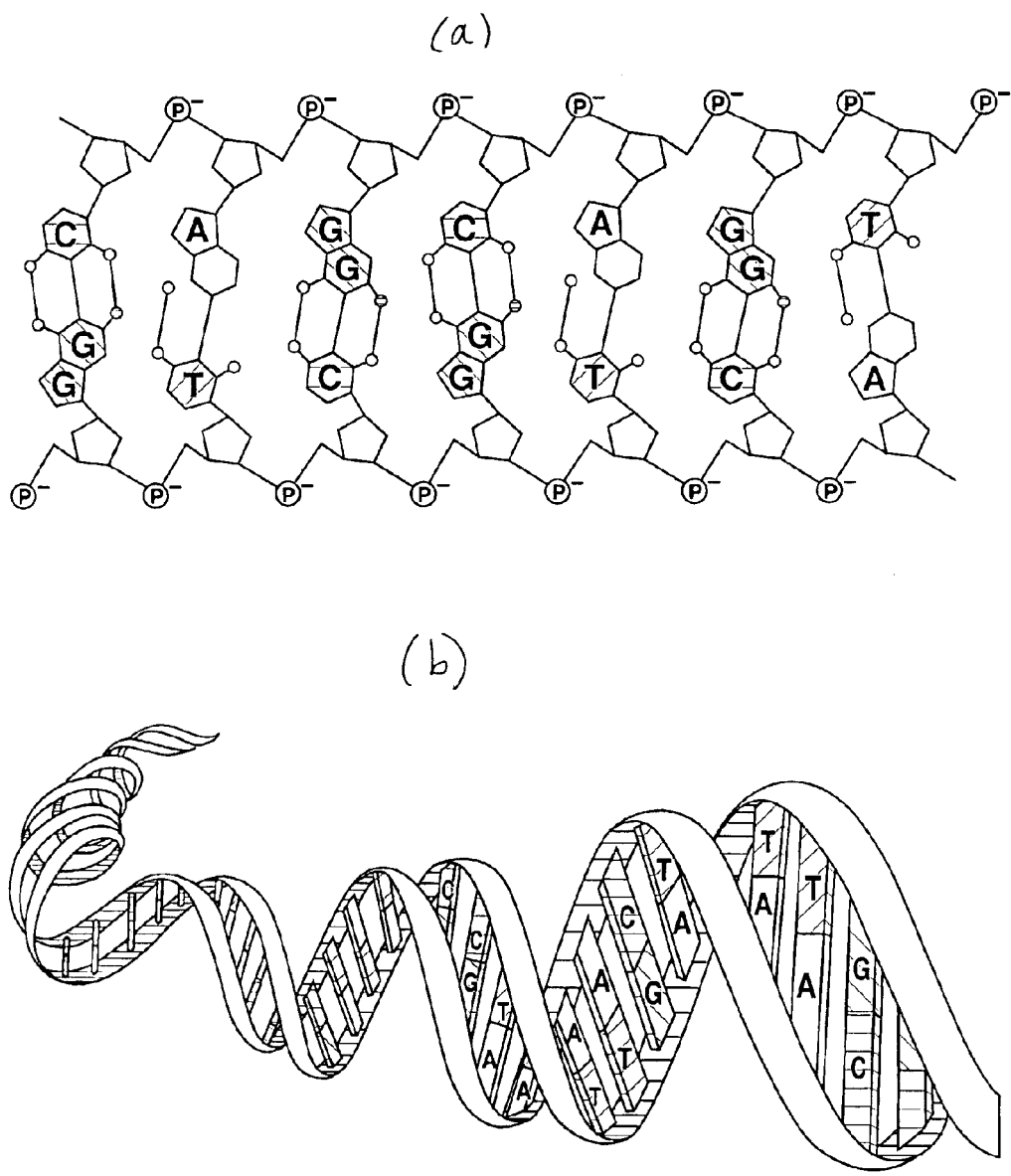
FIG. 5a is an illustration of the chemical structure for a section of a double-stranded DNA molecule.
FIG. 5b is an illustration of a DNA in a double helix form.
Figure 6:
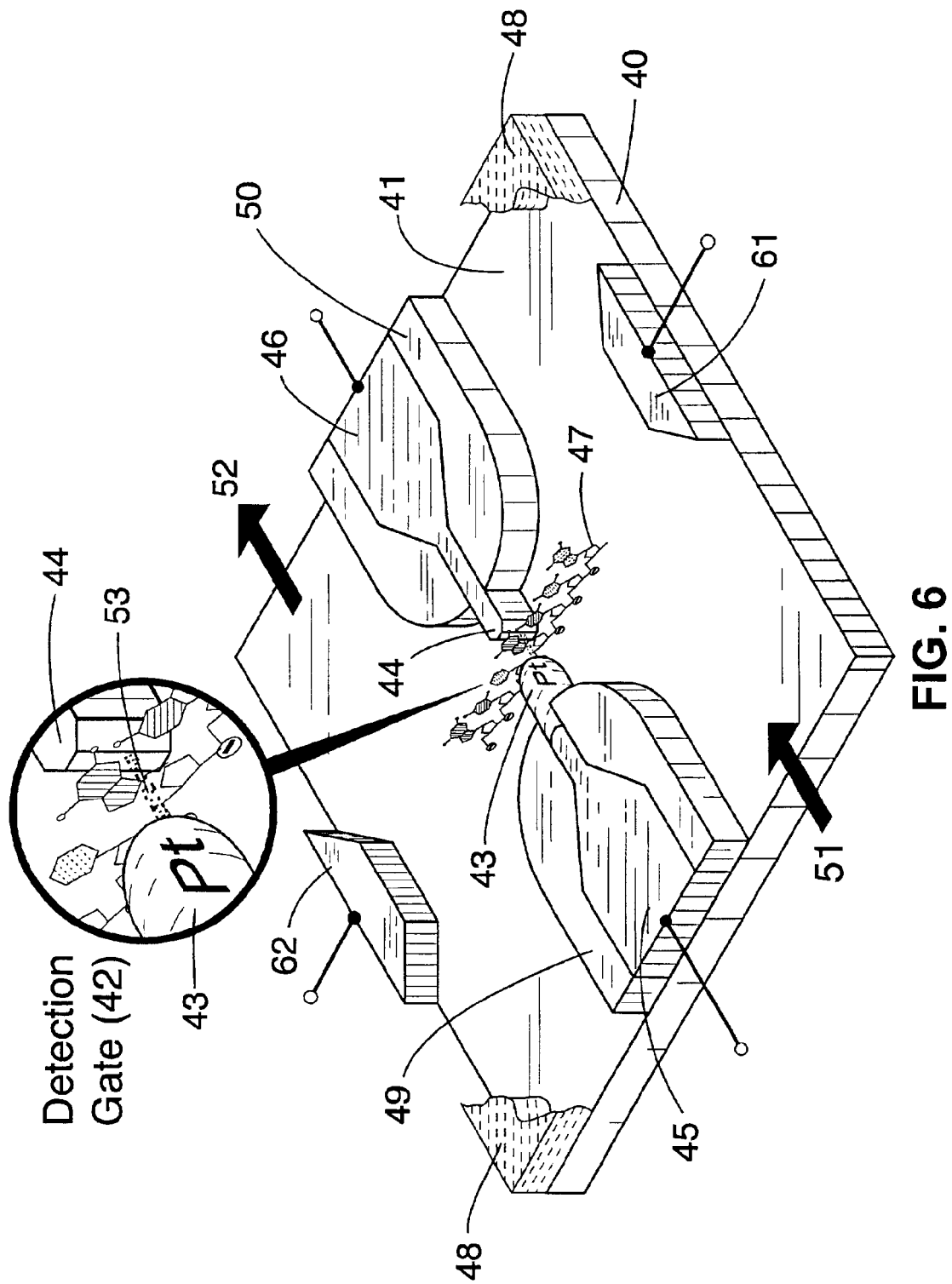
FIG. 6 is an illustration of a first embodiment of a DNA/RNA sequencing system that features nanoelectrode-gated molecular reading in a water or other liquid on a hydrophilic and nonconductive substrate surface.

A first embodiment of our invention is shown in FIG. 6. In FIG. 6, a sample plate or substrate 40 has a hydrophilic and nonconductive (e.g., silicon oxide) surface 41. A nucleotide detection gate 42 is shown in the inset. Also called a nanoelectrode detection gate or nanogate, the nucleotide detection gate 42 is defined as the distance between two precision nanotips 43, 44 of two detection electrodes (nanoelectrodes) 45, 46 respectively, pointing toward each other on the substrate surface 41. A controlled thin layer of water or other liquid 48 on the hydrophilic substrate surface 41 facilitates the loading and delivery of a DNA or RNA molecule through the nanoelectrode detection gate 42. The spacing (nanogap) between the two nanotips 43, 44 of the nanoelectrodes 45, 46 only has to be sufficient (in a range of about 2–6 nm) for passage of a single nucleic acid (DNA or RNA) molecule 47. The specific requirement for nanogap size is also dependent on the temperature and solvent conditions such as the pH and ionic strength of the water or liquid layer 48. To achieve the needed resolution for detection of an individual nucleotide (base) of the DNA molecule 47, the tips 43, 44 of the nanoelectrodes 45, 46 must be relatively sharp. This requirement can be met by fine-tuning the nanogap size and the nanotips through the method of programmable pulsed electrolytic metal deposition and depletion described earlier.

Figure 8:
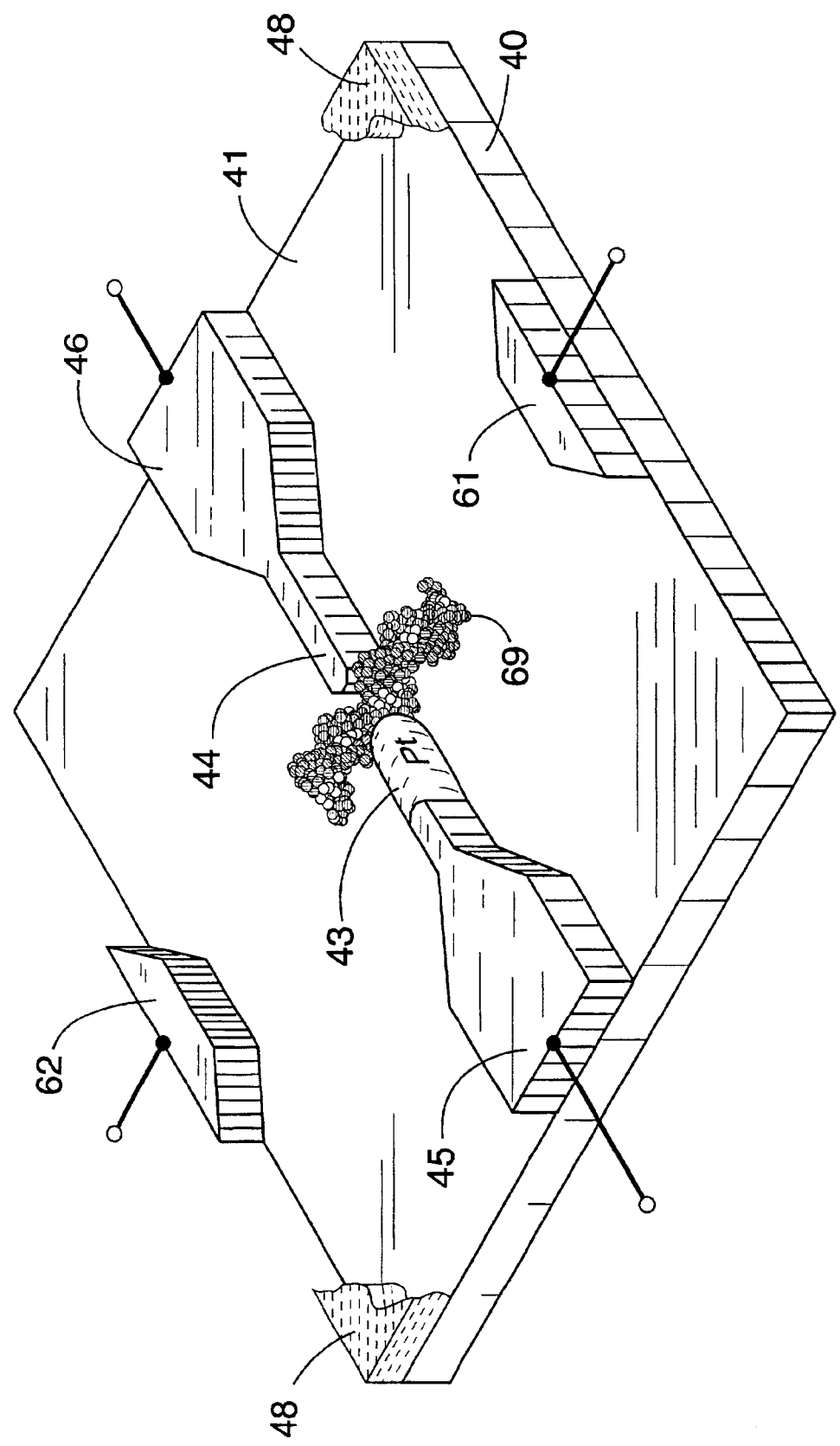
FIG. 8 is an illustration of a double-stranded DNA molecule positioned in the detection gate of the embodiment of FIG. 6.

When the distance between the nanoelectrode tips 43, 44 is within about six nanometers, significant electron tunneling across the nanogate 42 can occur with application of a tunneling biased voltage (V) across the nanogate 42. In an aqueous solution (water), the width of a single-stranded DNA molecule is about 2–3 nm (including some bound water molecules), while that of a double-stranded DNA is about 3–4 nm. FIG. 8 illustrates a double-stranded molecule 69 properly positioned in the nanogate for sequencing. A nanogap size of about 1–10 nm, preferably about 2–6 nm, between the nanoelectrode tips 43, 44, is sufficient for the passage of either type of DNA chain, and for detection by tunneling current measurement.

In FIG. 6, the thickness of the adsorbed water or liquid layer 48 increases with increasing humidity. By controlling the relative humidity, the thickness of the water layer 48 can be manipulated. In addition, by using specific types of surfaces or chemically modified ones, the water adsorption, and thus the thickness of the water layer, can be enhanced. It is possible to maintain a water layer with a thickness that is comparable to that of a single- or double-stranded DNA molecule.

In FIG. 6, protective insulating shields 49, 50, made of a nonhydrophilic and nonconductive material such as SiN, are constructed on the hydrophilic and nonconductive substrate surface 41 along the sides of the detection electrodes 45, 46, respectively. The shields 49, 50 are shaped such that only the nanoelectrode tips 43, 44 remain exposed on the substrate surface.

The shields 49, 50 serve at least three different functions. They provide physical protection of the nanoelectrodes 45, 46 while making the nanoelectrode tips 43, 44 more rigid on the substrate. They also minimize the Faraday current leakage from the nanoelectrodes 45, 46, i.e., they electrically insulate, or shield, the sides of the nanoelectrodes 45, 46 from the Faraday leakage current. Third, the shields help shape the passageway through the detection gate 42 for improved flow of the DNA/RNA molecule while preventing the molecule from contacting the sides of the nanoelectrodes 45, 46.

In FIG. 6, the nucleic acid sample is loaded into the apparatus in the sample loading area 51 using a micro/nanofluidic injection device, not shown. The sample-loading area 51 can be enlarged for manual injection of a DNA/RNA sample using a pipette. This is illustrated later in FIG. 13. After the DNA/RNA sample is loaded into the apparatus, it is delivered to the detection gate 42 by a pair of electrophoresis electrodes, i.e., the cathode macroelectrode 61 and the anode macroelectrode 62. After sequence detection, the sample can be removed from the system through the sample drain area 52.

Precise control of the DNA or RNA movement through the nanoelectrode detection gate 42 is an essential feature of this invention. Likewise, reliable detection of the DNA or RNA sequence at the nanogate 42 depends on being able to precisely control the movement of the DNA or RNA molecule through the nanogate. As shown in FIG. 6 and more particularly in FIG. 7, this control is achieved through the use of two programmable and perpendicular electric fields in conjunction with the water or liquid layer 48. The first is an electrophoresis electric field that is parallel to the sample plate 40 and is applied through the pair of electrophoresis electrodes 61, 62. The electrophoresis electrodes 61, 62 are fabricated on the substrate surface 41, and are aligned with the nanometer detection gate 42 on the substrate surface.

The second field is a holding electric field that is perpendicular to the substrate surface 41 and is applied through two parallel conductive plates 64, 65 located above and beneath the sample plate 40, respectively. An electrophoresis pulse generator 63 achieves precise control of the electrophoresis electric field; i.e., its sign (direction), amplitude, and duration. Similarly, a holding pulse generator 66 achieves precise control of the holding electric field. Thus, the step size of the DNA (or RNA) movement through the nanogate 42 is controlled by the duration and amplitude of the electrophoresis electric field in conjunction with the perpendicular holding electric field. In the preferred practice of this invention, the actions of these two electric fields and the process of molecular detection are synchronized and coordinated to achieve the ultrafast DNA/RNA sequencing.

As mentioned, the electrophoresis electric field moves the nucleic acid molecule 47 into and through the detection gate 42 in the thin layer of adsorbed water 48. Since the thickness of the water layer can be adjusted to allow movement of single molecules, it is possible to deliver a single nucleic acid molecule to the detection gate by electrophoresis through the nanofluidic layer.

Since both DNA and RNA have negatively charged chains of phosphate groups, the sample molecule will move toward the anode macroelectrode 62 under the influence of the electrophoresis electric field. The step size of the DNA or RNA movement is controlled by the duration and amplitude of the electrophoresis pulse. To provide sufficient time and stability for the nanoelectrodes 45, 46 to detect a DNA or RNA nucleotide (base) at the detection gate 42, the electrophoresis field is pulsed and stopped for the detection period after the base enters the detection gate 42.

With the holding electric field at the proper strength, and in the correct direction, i.e., the plate 65 beneath the sample plate 40 positively charged, there are two important results. First, the holding electric field is able to prevent any potential drift of the DNA molecule, and second, is able to hold a single-stranded DNA molecule with its phosphate groups down on the surface of the sample plate, and its nucleotides pointing upward as desired for base detection. This helps achieve a reliable and reproducible reading of a DNA sequence.

Figure 11:
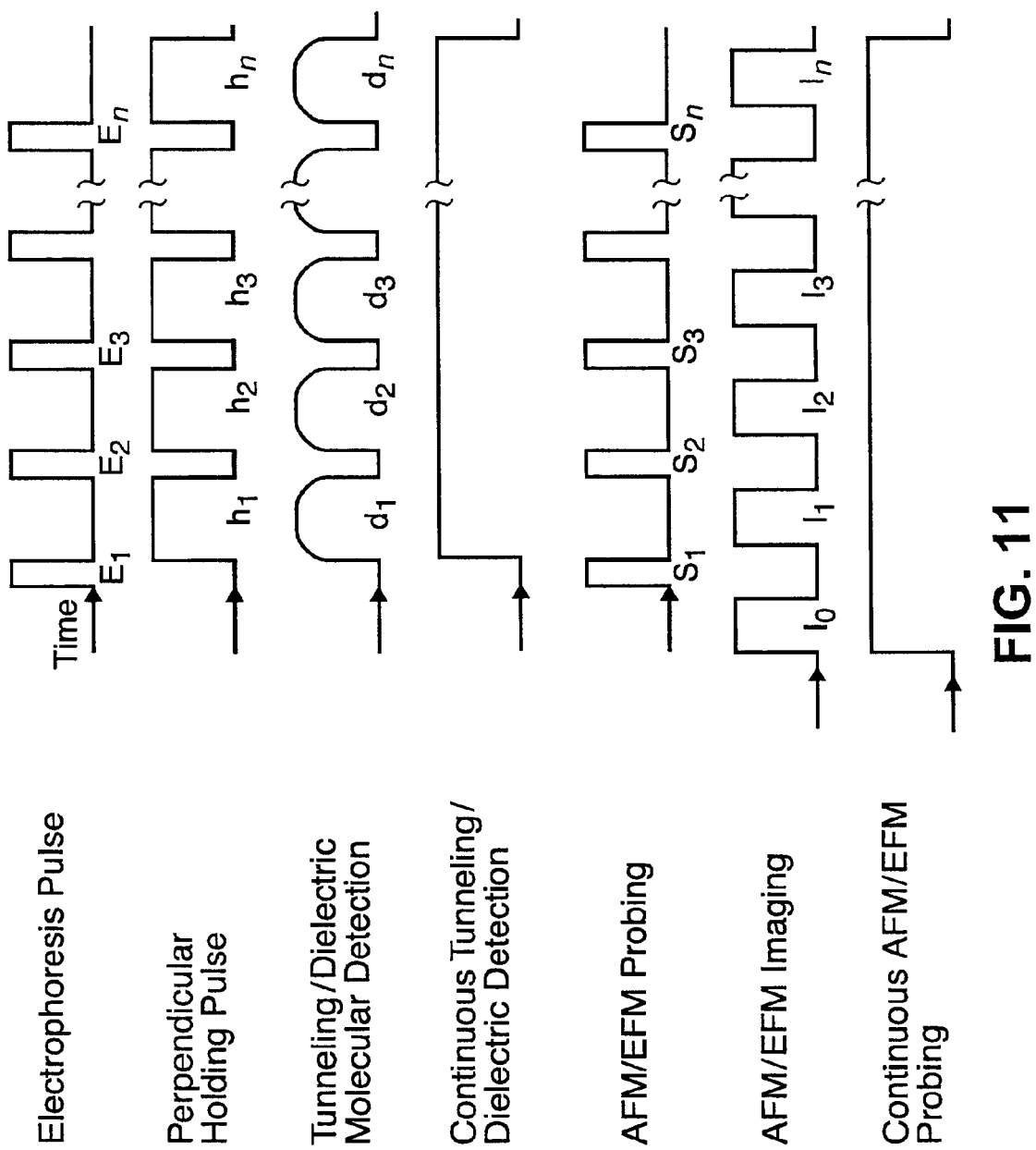
FIG. 11 is an illustration of the synchronization and coordination of electrophoresis and perpendicular holding electric fields, tunneling current detection, dielectric molecular detection, and atomic force microscopy (AFM)/electrostatic force microscopy (EFM) probing.

To achieve a coordinated process, various molecular detection processes are synchronized to the actions of the electrophoresis field and perpendicular holding field, as illustrated in FIG. 11.

Figure 7:
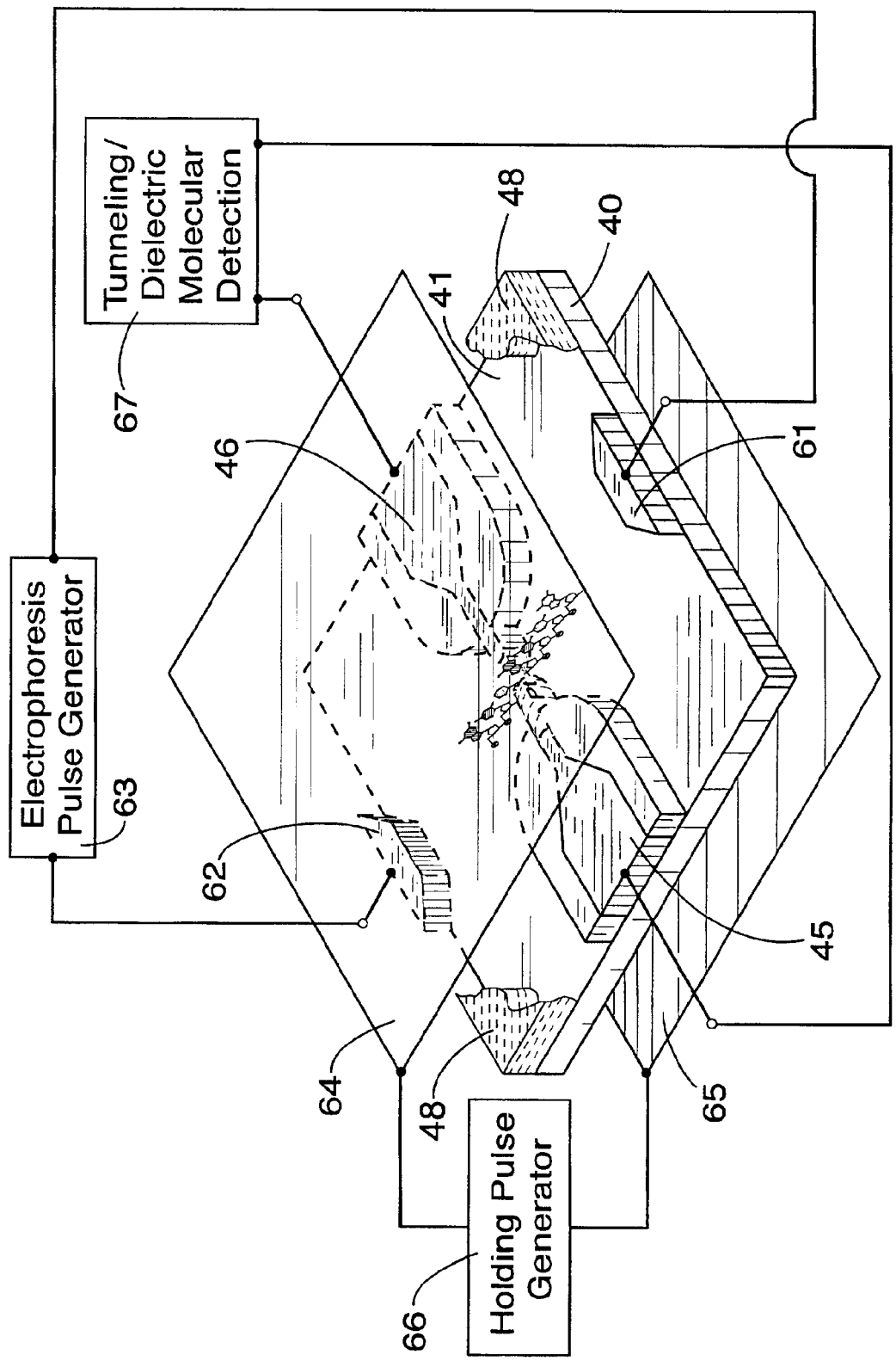
FIG. 7 is an illustration showing additional features of the embodiment of FIG. 6.

In FIGS. 6 and 7, the first molecular detection process we describe is measurement of tunneling current across the detection gate 42. This is illustrated at 67 in FIG. 7. Since the chemical compositions and structures of the four distinct nucleotides are different, the screening effect of each distinct nucleotide on the tunneling current (I) and tunneling characteristics (such as the tunneling I-V and/or [dI/dV]-V curves) is different.

Therefore, by detecting the difference in tunneling current (I) and/or tunneling characteristics (I-V and/or [dI/dV]-V curves) for each DNA nucleotide (base) passing through the detection gate, the sequence of a DNA molecule can be determined. Using some DNA molecules of known sequence, this detection system can be calibrated. A unique tunneling characteristic profile can then be established for each distinct DNA base. This tunneling profile is then used as a fingerprint to identify an individual base. With the ability to move a DNA molecule through the detection gate in a well-controlled manner, reliable sequence information can therefore be obtained at a speed much faster than the current DNA sequencing technology. Since the tunneling electrons likely emerge from a single (or a few) atom(s) of one nanoelectrode tip, and tunnel through the nanogap 42 to the tip of the other nanoelectrode for the shortest possible distance, the size of the tunneling electron beam is likely to be within a few angstroms (a fraction of a nanometer). This is sufficiently fine to make precise detection of an individual nucleotide of the DNA molecule possible. Therefore, the tunneling detection method can offer a better resolution than that of atomic force microscopy (AFM) probing, described below. The tunneling current method should be able to perform DNA sequencing on either single-stranded or double-stranded DNA molecules.

Besides tunneling current measurement, nanoelectrode-gated dielectric measurement (illustrated at 67 in FIG. 7 and also in FIGS. 9a, 9b) and atomic force microscopy (AFM)/electrostatic force microscopy (EFM) probing (shown in FIG. 10) are additional methods for detection of nucleic acid sequences that can be used with this invention.

Figure 9A:
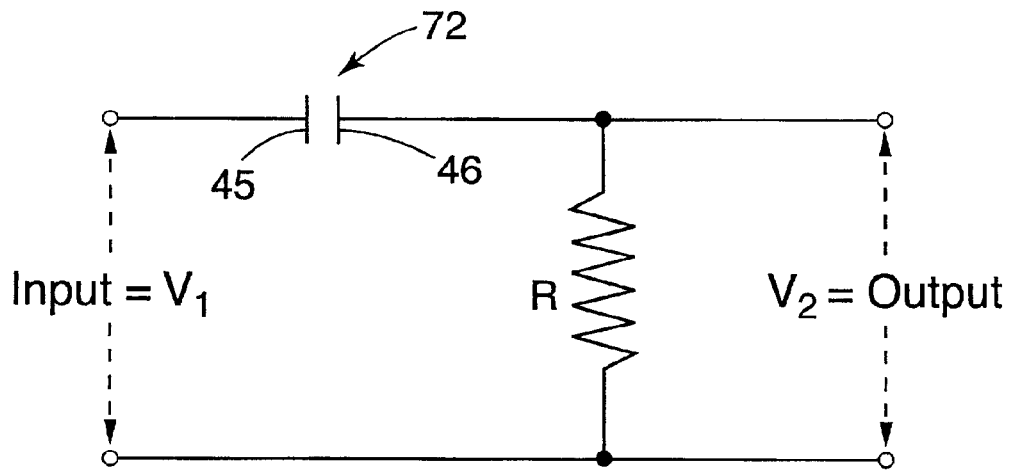
FIG. 9a is an illustration of a circuit used to detect DNA or RNA sequences by nanoelectrode-gated dielectric measurement.
Figure 9B:
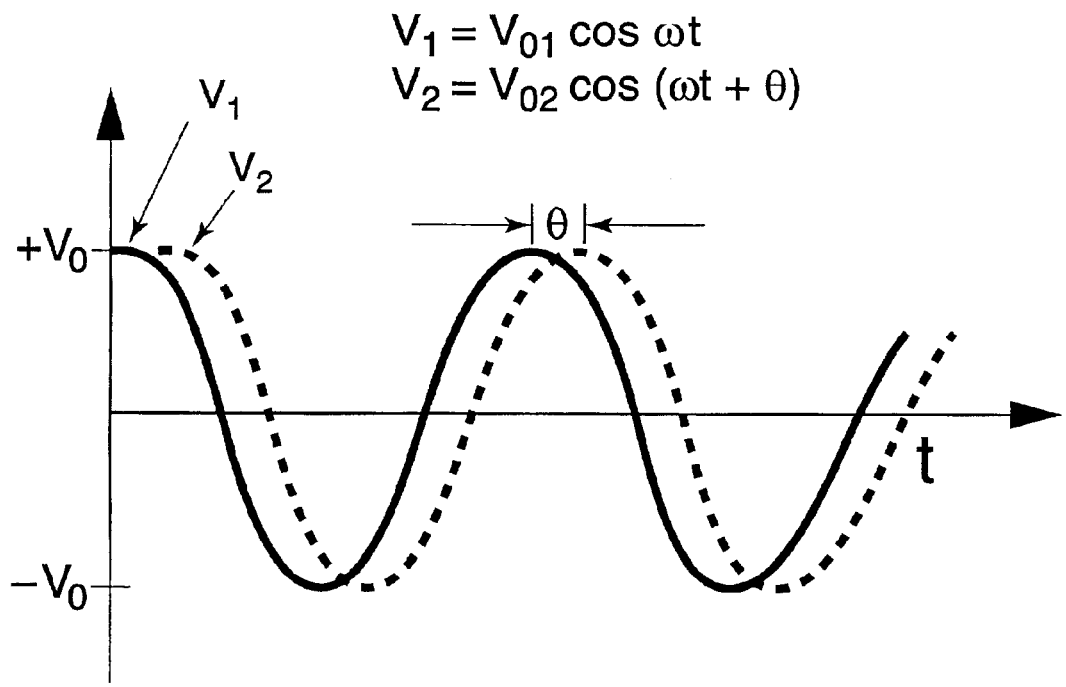
FIG. 9b is a graph illustrating the phase shift θ between the input ac voltage $V_1$ and the output voltage $V_2$ from this circuit used to detect a nucleic acid sequence.

In FIGS. 6 and 9, when the tips of the two nanoelectrodes 45, 46 are placed in close proximity to each other, they can act as elements of a parallel plate nanocapacitor 72 (FIG. 9a). An alternating voltage (ac voltage) applied between the nanoelectrodes 45, 46 will show a phase lag of 90° between the applied voltage and measured current. When a dielectric material such as a nucleic acid molecule is present between the nanoelectrodes, the phase lag varies as a function of the dielectric constant of the dielectric material. This phenomenon explains why the invention is capable of detecting the DNA or RNA sequence through the dielectric measurement of nucleic acid bases at the nanoelectrode gate 42. The capacitance of the parallel plate nanocapacitor 72 is dependent on the dielectric constant of the molecule and liquid 48 that are between the nanoelectrodes 45, 46.

The four DNA nucleotides (thymine, adenine, cytosine, and guanine) have different structures and compositions. Therefore, the dielectric constants of these nucleotides should be different. Another factor contributing to differences in dielectric constant is the interaction between the DNA and solvent (for example, water) molecules. Some water molecules are bound or semi-bound around the DNA chain. These water molecules have less freedom for rotation and are thus less polarizable than the free water molecules in a bulky phase. Consequently, the dielectric constant of the bound or semibound water molecules is significantly smaller than that of free water molecules.

Since each of the nucleotides has a somewhat different orientation and spatial relation with the phosphate chain, the geometry of the bound or semi-bound water molecules around each distinct nucleotide is also somewhat distinct. This distinct geometry can confer different dielectric constants for each base (thymine, adenine, cytosine, and guanine). The difference in dielectric constant can translate to a difference in the capacitance for the nanoelectrodes if the nanoelectrode tips are sharp enough and within an appropriate distance (nanometer range) of the chain of the DNA molecule.

With a proper electronic circuit as shown in FIG. 9a, it is possible to detect the difference in capacitance by measuring the phase shift ($\theta$) between an input ac voltage ($V_1$) and an output voltage signal ($V_2$). This is because the phase shift is a function of the capacitance (C) at a proper ac frequency ($\omega$) and impedance (R):

$$\theta = \tan^{-1}(1/\omega RC).$$

By using some DNA molecules of known sequence, calibration of the dielectric measurement system is possible. A unique phase-shift profile can be established for each distinct DNA base. This profile can be used as a fingerprint to identify an individual base. With the ability to move a DNA molecule through the detection gate 42 in a well-controlled manner, reliable sequence information can be obtained at a speed that can be about 2800 times faster than that available with current DNA sequencing technology. The dielectric measurement method is capable of performing DNA sequencing on both single-stranded and double-stranded DNA molecules.

FIG. 9 also shows that measurement of the phase shift ($\theta$) between the input ac voltage ($V_1$) and output voltage signal ($V_2$) can be achieved within the time of one cycle of the ac signals. Since the frequency of the input ac voltage ($V_1$) can be in the megahertz (MHz) range, the reading of a nucleotide base by dielectric detection can be completed within a microsecond. By use of the programmable electric fields described in this invention, it is possible to move a DNA molecule through the detection gate at a speed of about 1 base per nanosecond. Therefore, this nanotechnology-based sequencing system can theoretically have a maximal sequencing rate of about 1,000,000 bases per second. With all considerations of practical operations, it is estimated that this nanotechnology system should be able to perform DNA sequencing on a single DNA molecule at a speed at least 2800 times faster than that available through the current DNA sequencing technology.

Figure 10:
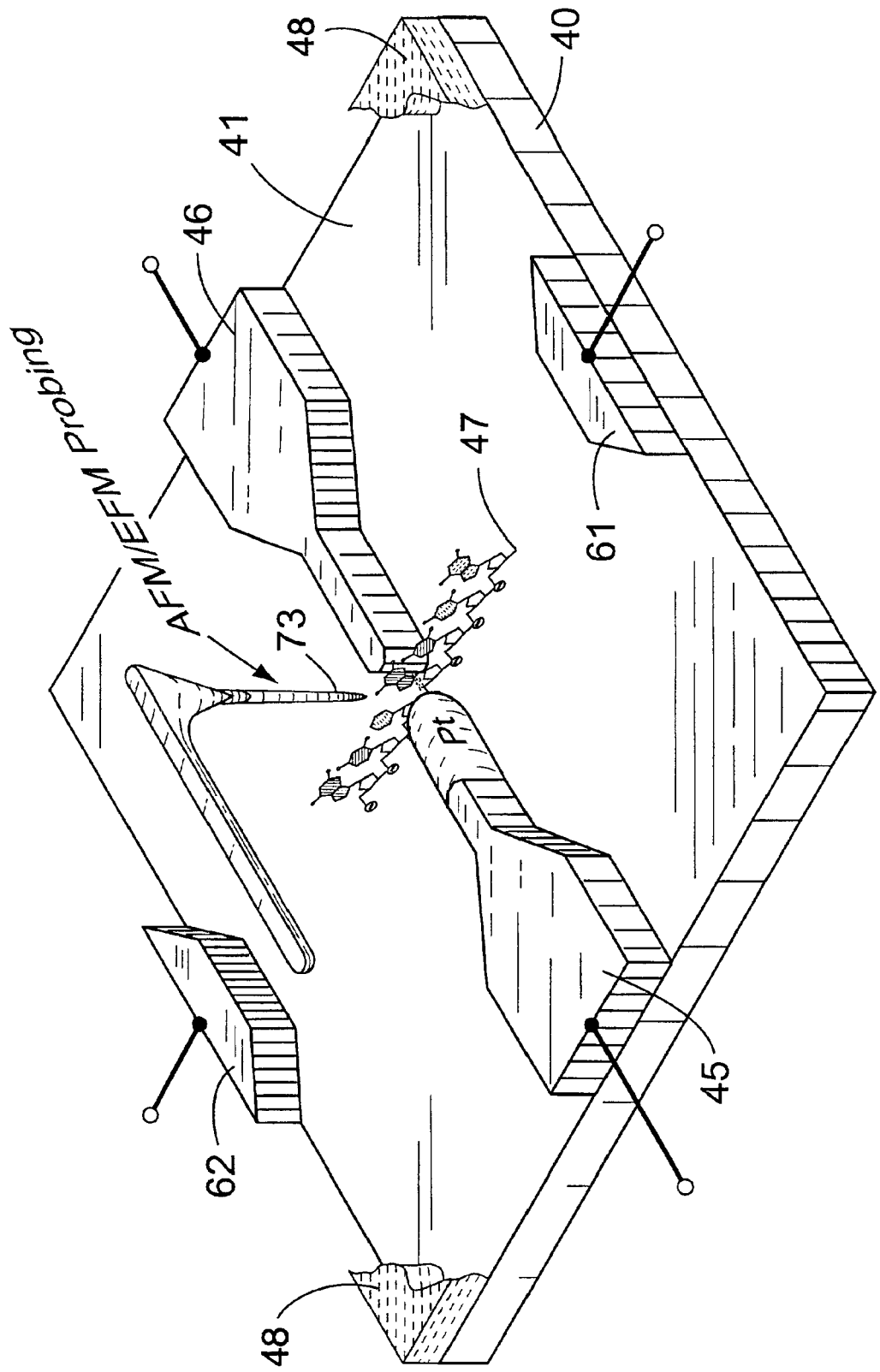
FIG. 10 is an illustration of the use of atomic force microscopy (AFM) and/or electrostatic force microscopy (EFM) to probe a nucleic acid molecule.

FIG. 10 illustrates that atomic force microscopy (AFM) or electrostatic force microscopy (EFM) probing is yet another method that can be used to probe a nucleic acid molecule in this invention. In FIG. 10, AFM probing with a sharp tip 73 is shown probing the DNA or RNA molecule 47 at the detection gate. The AFM probing can be used to determine whether a nucleic acid molecule is present. An AFM tip that is sufficiently fine (such as one made of a carbon nanotube) may be able to detect certain characteristic differences between some bases and DNA domains. However, conventional AFM imaging so far has not been able to resolve individual base structures. Thus, at present, AFM probing can aid in sequencing detection but would not be sufficient to obtain complete sequencing information.

As mentioned earlier, for single-stranded DNA, the phosphate chain can be pulled to the bottom surface by the holding electric field, allowing its nucleotides to be turned upward at the detection gate. This configuration is perfect for an AFM probe to obtain characteristic scanning profiles for the DNA nucleotides. The tapping mode of AFM operation may be preferred to ensure that no undesirable drag of the molecule by the AFM tip occurs. In FIG. 10, a time-dependent probing profile can be obtained by using the AFM tip 73 to scan on top of the DNA molecule 47 back and forth in the nanoelectrode 45, 46 direction while the DNA molecule moves through the detection gate in the macroelectrode 61 or 62 direction during the pulsed electrophoresis. When the speed of the DNA movement under a given electrophoresis electric field is known, an image file can be reconstructed from the time-dependent AFM probing files.

The velocity of the DNA movement during the electrophoresis period can be determined by comparative analysis of the time-dependent profile with standard AFM images that can be obtained while the molecule is held steadily at the gate by the holding electric field. The velocity information can be useful in adjusting the strength and duration of the electrophoresis electric field to achieve the desired speed of the DNA movement for the sequence detection. The detection system can be calibrated with some DNA molecules of known sequence. A characteristic AFM probing profile can be established for certain DNA bases or domains. This type of profile can then be combined with tunneling current and other detection profiles, and become an aid to the sequence determination.

FIG. 10 also illustrates that the DNA nucleotides can be detected by EFM probing. The addition of acid or alkali to the water layer 48 can ionize the bases of a DNA molecule. The charge density of a base may differ with each distinct nucleotide at certain pH conditions. Therefore, the use of EFM probing can potentially help to identify the nucleotides. The objective is to obtain some distinct signals from the EFM probing that can be used to identify the four distinct nucleotides. EFM probes having a sharp tip that is doped with a single-charged atom are now available. This type of EFM tip should have a resolution that is sufficiently fine to probe a nucleotide of the DNA molecule. Preferably, the EFM probing should be operated in the tapping mode to achieve optimal detection sensitivity.

Figure 12:
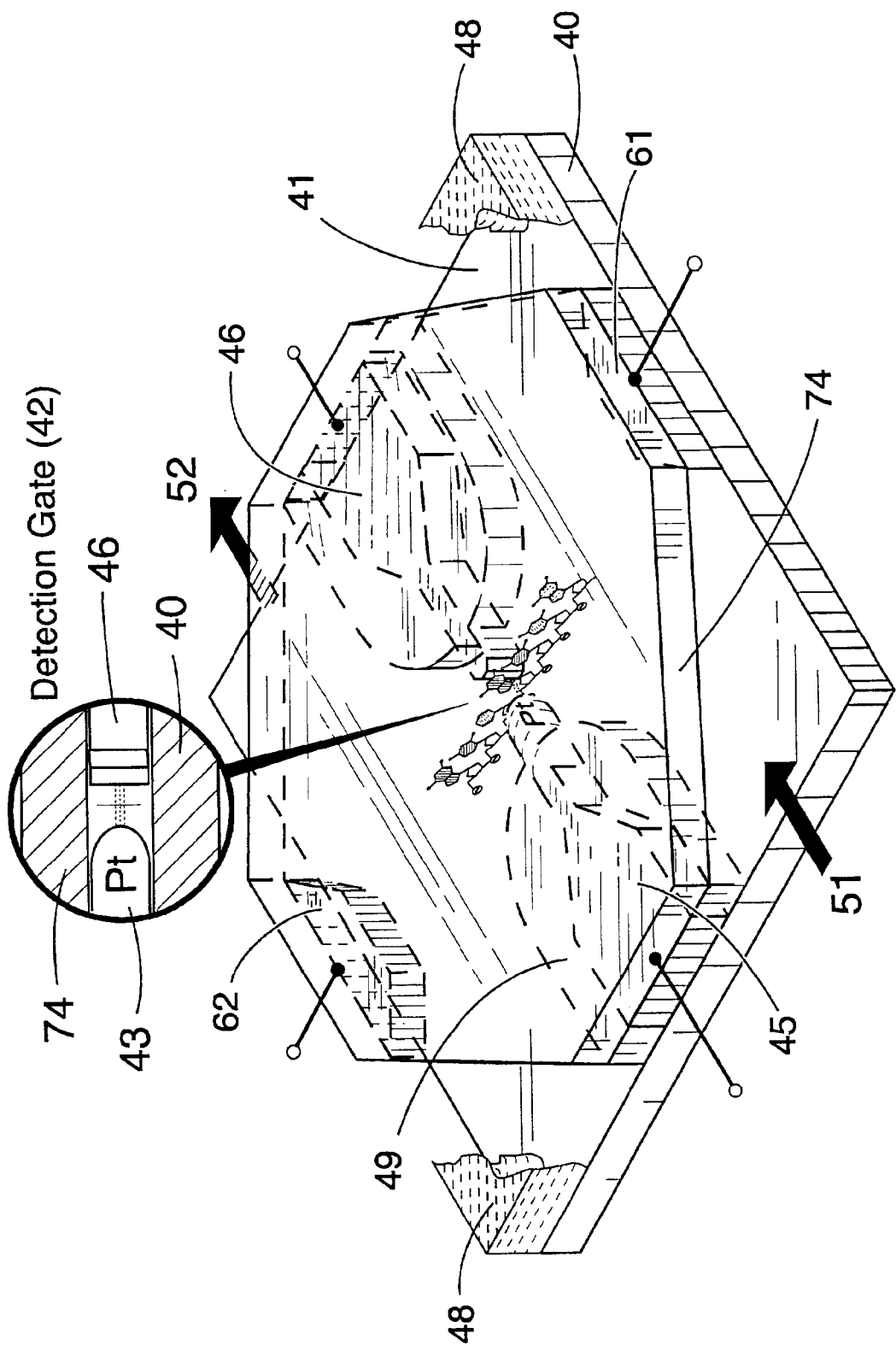
FIG. 12 is an illustration of a second embodiment of a DNA/RNA sequencing system that features a closed channel for conveyance of the water or liquid containing the nucleic acid molecule(s).

Another embodiment of the invention is shown in FIG. 12. In FIG. 12, the thickness of the liquid 48 is controlled by a hydrophilic and nonconductive cover 74 mounted on the nanoelectrodes 45, 46, protective shields 49, 50 and electrophoresis electrodes 61, 62. The cover 74 forms a confined space for the liquid, and also a channel for flow of the sample and liquid from the sample loading area 51 through the detection gate 42 to the sample drain area 52. The DNA would be mixed with the liquid and both injected into the apparatus. Alternatively, the liquid could fill the volume between the hydrophilic substrate 41 and the hydrophilic cover 74. In the embodiment of FIG. 12, there is no need to provide the relative humidity control system, or to maintain the liquid 48 level as in the previous embodiment. The liquid 48 fills the space between the substrate surface 41 and the cover 74.

Figure 13:
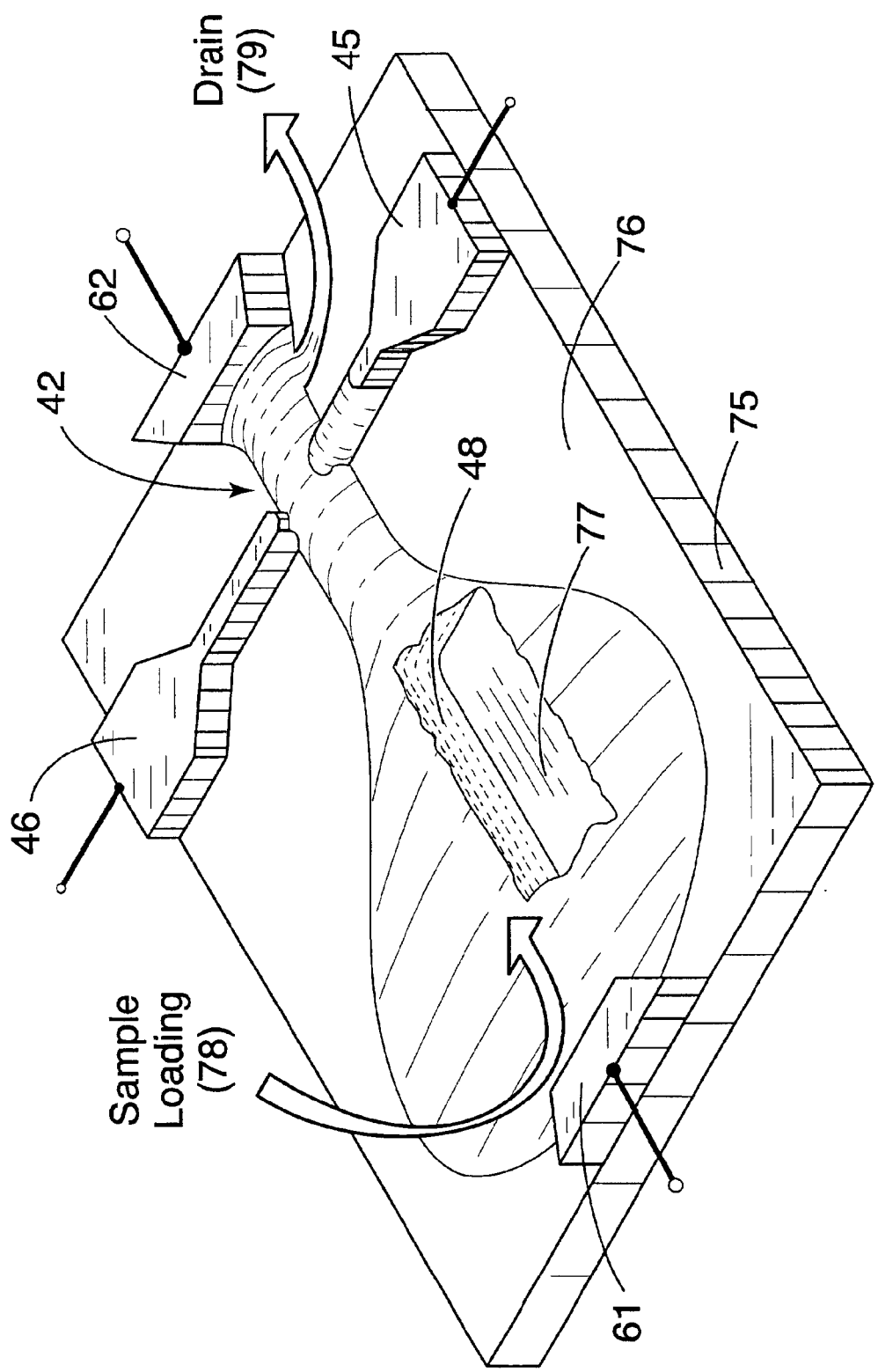
FIG. 13 is an illustration of a third embodiment of a DNA/RNA sequencing system that includes a funnel-like microfluidic water column to deliver the nucleic acid molecule to the detection gate.

Still another embodiment of the invention is shown in FIG. 13. In the earlier embodiment, the action of microfluidics and electric fields on a hydrophilic (e.g., silicon oxide) plate was used to load and deliver the DNA/RNA molecule into the detection gate for sequence detection. FIG. 13 illustrates how the molecular delivery capability of the invention can be enhanced. In this figure, the nanoelectrodes 45, 46, electrophoresis electrodes 61, 62, nanoelectrode detection gate 42, and sample loading 78 and drain area 79 function the same as described earlier.

However, in FIG. 13, the surface 76 of the sample plate 75 is a hydrophobic and nonconductive surface, the length of the region between the cathode macroelectrode 61 and the detection gate 42 is extended, and the portion 77 of the substrate surface between the macroelectrodes 61, 62 is constructed as a hydrophilic and nonconductive region. In a controlled humidity environment, the water vapor tends to condense preferentially in the hydrophilic region 77 rather than on the hydrophobic surface 76. This causes the formation of a raised, nanometer-scale, funnel-like water column 48 as illustrated on the hydrophilic region 77 between the macroelectrodes 61, 62. The raised funnel-like water column 48 is effective for loading and delivery of a DNA or RNA molecule to the detection gate 42. The thickness of the funnel-like aqueous column can be adjusted by controlling the ambient humidity so that a single nucleic acid molecule can be electrophoresized into and through the detection gate 42.

The hydrophilic region 77 can be constructed by producing hydrophilic lines or a hydrophilic area on the hydrophobic substrate surface 76. This can be achieved by using photolithography with lasers or other micro/nanolithographic techniques. For example, a monolayer of hydrophobic molecules can be deposited on a substrate. Lines of these hydrophobic molecules can then be desorbed by using a laser beam or AFM tip. Therefore, it is possible to make hydrophilic lines of any shape on a substrate surface using simple lithographic techniques. This can also be done using contact printing technology. The width of these lines is in the micron or nanometer range. By use of nanoscale tools such as an AFM tip, hydrophilic lines with nanometer width can be produced.

Once such hydrophilic lines or areas are made, they can be placed in a chamber where the humidity can be controlled very accurately. The water vapor condenses along the hydrophilic lines at certain levels of relative humidity. The thickness of the water layer 48 depends on the relative humidity and temperature. In practice, the substrate can be rinsed in an aqueous solution containing appropriate salts.

For the embodiment of FIG. 13, the lithographic patterns are such as to produce a larger sample loading area 78 and possibly a larger drain area 79 in order to make the sample loading and removal more convenient. In this way, loading of a nucleic acid sample can be achieved using a number of available techniques including but not limited to micropipetting, microfluidic, and/or nanofluidic injection. After the nucleic acid sample is placed in the sample loading area 78, the sample molecule will move through the funnel-like delivery water column 48 on the hydrophilic region 77, and will enter the nanoelectrode gate 42 when a voltage difference is applied across the macroelectrodes 61, 62. The molecule can then be detected by the tunneling current and/or dielectric measurement methods described earlier.

Each of the four distinct nucleotide bases has a somewhat different $pK_a$ value or different affinity to certain solvent molecules. It should be possible to make the DNA nucleotides more detectable by controlling the solvent conditions. For example, by adjusting the pH of the solvent, it is possible to ionize only certain types of bases. This technique allows the detection of specific types of bases by the EFM probing technique. When it is desired, certain nucleotides may be chemically modified (such as by methylation) to allow easier detection by the probing techniques described herein.

In order to achieve the optimal performance of this nanotechnology, multiple detection gates may be used in serial and/or in parallel so that all or any combination of the DNA nucleotide detection techniques can be employed. The actions of the perpendicular electric fields and the nucleotide detection processes should be coordinated as illustrated in FIG. 11 through computerized system control and data acquisition. A characteristic profile of the probing signals can be established for each of the four distinct DNA nucleotides by probing the nucleotides of a DNA molecule of known sequence through all or any combination of the detection techniques. These characteristic signal profiles can then be used to identify the DNA sequence through computer data fitting.

While there has been shown and described what are at present considered the preferred embodiments of the invention, it will be obvious to those skilled in the art that various changes and modifications can be prepared therein without departing from the scope of the inventions defined by the appended claims.

We claim:

1. A nanoscale nucleic acid sequence detection apparatus comprising:
   a) a hydrophilic nonconductive substrate serving as a sample plate;
   b) a cathode macroelectrode located on one surface of said substrate;
   c) an anode macroelectrode located on said surface of said substrate such that the spacing between said cathode macroelectrode and said anode macroelectrode is greater than the length of one nucleic acid molecule, the spacing between said cathode macroelectrode and said anode macroelectrode defining a nucleic acid loading and delivery path;
   d) a molecular transport liquid located on said surface of said substrate;
   e) an injection device capable of introducing a sample nucleic acid molecule into said molecular transport liquid;
   f) a programmable pulse generator connected to said cathode macroelectrode and said anode macroelectrode, said programmable pulse generator capable of controllably moving a nucleic acid molecule contained in said liquid along the nucleic acid loading and delivery path between said cathode macroelectrode and said anode macroelectrode by means of a programmable electrophoresis electric field;
   g) a first nanoelectrode located on said surface of said substrate;
   h) a second nanoelectrode located on said surface of said substrate such that the gap between said first nanoelectrode and said second nanoelectrode crosses the nucleic acid loading and delivery path, the gap between said first nanoelectrode and said second nanoelectrode defining a nanometer-size nucleic acid detection gate on said hydrophilic nonconductive substrate;
   i) a first nonhydrophilic and nonconductive protective insulating shield constructed on said surface of said substrate along the sides of said first nanoelectrode, the construction of said first protective insulating shield such that only a tip of said first nanoelectrode remains exposed on said surface of said substrate;
   j) a second nonhydrophilic and nonconductive protective insulating shield constructed on said surface of said substrate along the sides of said second nanoelectrode, the construction of said second protective insulating shield such that only a tip of said second nanoelectrode remains exposed on said surface of said substrate; and
   k) a nucleic acid nucleotide base detection means located at said nucleic acid detection gate.

2. The apparatus of claim 1, further comprising:
   two parallel spaced-apart electrically conductive plates, said plates arranged such that said sample plate is located between said electrically conductive plates; and
   a second programmable pulse generator connected to said electrically conductive plates, said second programmable pulse generator capable of applying a holding electric field across said conductive plates in order to orient the nucleic acid molecule contained in said liquid with respect to said sample plate and said conductive plates.

3. The apparatus of claim 1 wherein said injection device is a micropipette, a microfluidic injection device, or a nanofluidic injection device.

4. The apparatus of claim 2 wherein the movement and orientation of a sample nucleic acid molecule is precisely controlled by coordinated action of said programmable electrophoresis electric field and said holding electric field.

5. The apparatus of claim 1 wherein the moving direction and step size of a sample nucleic acid molecule at said detection gate is controlled by adjusting the direction, amplitude, and duration of the programmable electrophoresis electric field.

6. The apparatus of claim 2 wherein a sample nucleic acid molecule is oriented with its negatively charged chain of phosphate groups pointing downward toward the surface of the sample plate, and its nucleotide bases pointing upward as desired for detection by using the holding electric field at the proper strength and in the correct direction, i.e., the electrically conductive plate beneath the sample plate positively charged.

7. The apparatus of claim 2 wherein a sample nucleic acid molecule is held at said detection gate for a period by a holding electric pulse from said second programmable pulse generator delivered through said parallel electrically conductive plates so as to ensure reliable detection of the nucleotides.

8. The apparatus of claim 1 wherein the passage of a single nucleic acid molecule is achieved by use of detection gate spacing in the range of 1–10 nm.

9. The apparatus of claim 1 wherein the passage of a single nucleic acid molecule is achieved by use of detection gate spacing in the range of 2–6 nm.

10. The apparatus of claim 1 wherein the detection of a single nucleic acid molecule and reading of its nucleotide base sequence is achieved by use of a detection gate spacing in the range of 1–10 nm.

11. The apparatus of claim 1 wherein the detection of a single nucleic acid molecule and reading of its nucleotide base sequence is achieved by use of a detection gate spacing in the range of 2–6 nm.

12. The apparatus of claim 1 wherein said molecular transport liquid is provided and controlled by a relative humidity control system.

13. The apparatus of claim 1 further comprising a hydrophilic and nonconductive cover placed on the top sides of said macroelectrodes, said nanoelectrodes, and said protective shields to control the thickness of said molecular transport liquid on said hydrophilic nonconductive substrate.

14. The apparatus of claim 1 wherein said nucleic acid nucleotide base detection means is a tunneling current detector.

15. The apparatus of claim 1 wherein said nucleic acid nucleotide base detection means is a tunneling current spectroscope.

16. The apparatus of claim 1 wherein said nucleic acid nucleotide base detection means is a dielectric molecular detector.

17. The apparatus of claim 1 wherein said nucleic acid nucleotide base detection means is a high-resolution atomic force microscopic (AFM) probe.

18. The apparatus of claim 1 wherein said nucleic acid nucleotide base detection means is an electrostatic force microscopic (EFM) probe.

19. The apparatus of claim 1 wherein said molecular transport liquid is a chemical solution.

20. The apparatus of claim 1 wherein the passage of a single nucleic acid molecule and detection of its nucleotides is enhanced by use of appropriate solvent conditions such as pH and ionic strengths.

21. The apparatus of claim 2 wherein the actions of said nucleic acid nucleotide base detection and said electrophoresis and holding electric fields are coordinated and synchronized.

22. The apparatus of claim 1 wherein the apparatus is calibrated with standard nucleic acid samples of known sequences, and signal profiles of said sequences are established for each of the four distinct nucleotide bases: adenine (A), guanine (G), thymine (T) (uracil (U) if RNA), and cytosine (C).

23. The apparatus of claim 22 wherein the nucleotide sequence information of an unknown nucleic acid sample molecule is obtained by comparing its nucleotide base detection signals with said established signal profiles of said four distinct nucleotides with computer-assisted data fitting.

24. A nanoscale nucleic acid sequence detection apparatus comprising:

a) a hydrophobic and nonconductive substrate serving as a sample plate;

b) a cathode macroelectrode located on one surface of said substrate;

c) an anode macroelectrode located on said surface of said substrate such that the spacing between said cathode macroelectrode and said anode macroelectrode is greater than the length of one nucleic acid molecule, the spacing between said cathode macroelectrode and said anode macroelectrode defining a nucleic acid loading and delivery path;

d) a first nanoelectrode located on said surface of said substrate;

e) a second nanoelectrode located on said surface of said substrate such that the gap between said first nanoelectrode and said second nanoelectrode crosses the nucleic acid loading and delivery path, the gap between said first nanoelectrode and said second nanoelectrode defining a nanometer-size nucleic acid detection gate on said hydrophobic and nonconductive substrate;

f) a hydrophilic sample loading and delivery area on said hydrophobic and nonconductive substrate, said hydrophilic area extending along said nucleic acid loading and delivery path from said cathode macroelectrode to said anode macroelectrode, said hydrophilic sample loading and delivery area constructed so as to taper gradually less from said cathode macroelectrode to said nucleic acid detection gate;

g) a molecular transport liquid located on said hydrophilic sample loading and delivery area, said molecular transport liquid preferentially tending to form a funnel liquid delivery path on said hydrophilic sample loading and delivery area;

h) an injection device capable of introducing a sample nucleic acid molecule into said molecular transport liquid;

i) a nucleic acid nucleotide base detection means located at said nucleic acid detection gate;

j) a first programmable pulse generator connected to said cathode macroelectrode and to said anode macroelectrode, said first programmable pulse generator capable of controllably moving a nucleic acid molecule contained in said liquid along the nucleic acid loading and delivery path between said cathode macroelectrode and said anode macroelectrode by means of a programmable electrophoresis electric field;

k) two parallel spaced-apart electrically conductive plates, said electrically conductive plates arranged such that said sample plate is located between said electrically conductive plates; and l) a second programmable pulse generator connected to said electrically conductive plates, said second programmable pulse generator capable of applying a holding electric field across said electrically conductive plates in order to orient the nucleic acid molecule contained in said liquid with respect to said sample plate and said electrically conductive plates.

25. The apparatus of claim 24 wherein said injection device is a micropipette, a microfluidic injection device, or a nanofluidic injection device.

26. The apparatus of claim 24 wherein the movement and orientation of a sample nucleic acid molecule is precisely controlled by coordinated action of said programmable electrophoresis electric field and said holding electric field.

27. The apparatus of claim 24 wherein the moving direction and step size of a sample nucleic acid molecule at said detection gate is controlled by adjusting the direction, amplitude, and duration of the programmable electrophoresis electric field.

28. The apparatus of claim 24 wherein a sample nucleic acid molecule is oriented with its negatively charged chain of phosphate groups pointing downward toward the surface of the sample plate, and its nucleotide bases pointing upward as desired for detection by using the holding electric field in the proper strength and in the correct direction, i.e., the electrically conductive plate beneath the sample plate positively charged.

29. The apparatus of claim 24 wherein a sample nucleic acid molecule is held at said detection gate for a period by a holding electric pulse from said second programmable pulse generator delivered through said parallel electrically conductive plates so as to ensure reliable detection of the nucleotides.

30. The apparatus of claim 24 wherein the passage of a single nucleic acid molecule is achieved by use of detection gate spacing in the range of 1–10 nm.

31. The apparatus of claim 24 wherein the passage of a single nucleic acid molecule is achieved by use of detection gate spacing in the range of 2–6 nm.

32. The apparatus of claim 24 wherein the detection of a single nucleic acid molecule and reading of its nucleotide base sequence is achieved by use of a detection gate spacing in the range of 1–10 nm.

33. The apparatus of claim 24 wherein the detection of a single nucleic acid molecule and reading of its nucleotide base sequence is achieved by use of a detection gate spacing in the range of 2–6 nm.

34. The apparatus of claim 24 wherein said molecular transport liquid is provided and controlled by a relative humidity control system.

35. The apparatus of claim 24 wherein said nucleic acid nucleotide base detection means is a tunneling current detector.

36. The apparatus of claim 24 wherein said nucleic acid nucleotide base detection means is a tunneling current spectroscope.

37. The apparatus of claim 24 wherein said nucleic acid nucleotide base detection means is a dielectric molecular detector.

38. The apparatus of claim 24 wherein said nucleic acid nucleotide base detection means is a high-resolution atomic force microscopic (AFM) probe.

39. The apparatus of claim 24 wherein said nucleic acid nucleotide base detection means is an electrostatic force microscopic (EFM) probe.

40. The apparatus of claim 24 wherein said molecular transport liquid is a chemical solution.

41. The apparatus of claim 24 wherein the passage of a single nucleic acid molecule and detection of its nucleotides is enhanced by use of appropriate solvent conditions such as pH and ionic strengths.

42. The apparatus of claim 24 wherein the actions of said nucleic acid nucleotide base detection and said electrophoresis and holding electric fields are coordinated and synchronized.

43. The apparatus of claim 24 wherein the apparatus is calibrated with standard nucleic acid samples of known sequences, and signal profiles of said sequences are established for each of the four distinct nucleotide bases: adenine (A), guanine (G), thymine (T) (uracil (U) if RNA), and cytosine (C).

44. The apparatus of claim 43 wherein the nucleotide sequence information of an unknown nucleic acid sample molecule is obtained by comparing its nucleotide base detection signals with said established signal profiles of said four distinct nucleotides with computer-assisted data fitting.

* * * * *